(12) United States Patent
Craig

(10) Patent No.: US 7,740,878 B2
(45) Date of Patent: Jun. 22, 2010

(54) USE OF BETAINE TO ENHANCE EXERCISE PERFORMANCE

(75) Inventor: Stuart Andrew Shaw Craig, Somers, NY (US)

(73) Assignee: Danisco A/S, Copenhagen K (DK)

( * ) Notice: Subject to any disclaimer, the term of this patent is extended or adjusted under 35 U.S.C. 154(b) by 831 days.

(21) Appl. No.: 10/277,708

(22) Filed: Oct. 22, 2002

(65) Prior Publication Data

US 2003/0091615 A1 May 15, 2003

Related U.S. Application Data

(60) Provisional application No. 60/343,623, filed on Oct. 22, 2001.

(51) Int. Cl.
*A61K 47/00* (2006.01)
*A23K 1/30* (2006.01)

(52) U.S. Cl. .......................... 424/439; 426/72; 426/73; 426/74

(58) Field of Classification Search ................ None
See application file for complete search history.

(56) References Cited

U.S. PATENT DOCUMENTS

| 5,026,721 | A | * | 6/1991 | Dudrick et al. | 514/396 |
| 5,397,786 | A | * | 3/1995 | Simone | 514/300 |
| 6,117,872 | A | * | 9/2000 | Maxwell et al. | 514/249 |
| 6,368,617 | B1 | * | 4/2002 | Hastings et al. | 424/439 |
| 6,420,342 | B1 | * | 7/2002 | Hageman et al. | 514/23 |
| 6,429,198 | B1 | * | 8/2002 | St. Cyr et al. | 514/23 |
| 6,475,514 | B1 | * | 11/2002 | Blitzer et al. | 424/449 |
| 2002/0002146 | A1 | * | 1/2002 | Halevie-Goldman | 514/47 |
| 2002/0176881 | A1 | * | 11/2002 | Verlaan et al. | 424/439 |
| 2003/0211133 | A1 | * | 11/2003 | Meehan | 424/439 |

* cited by examiner

*Primary Examiner*—S. Tran
(74) *Attorney, Agent, or Firm*—Scully, Scott, Murphy & Presser, P.C.

(57) ABSTRACT

The present invention is directed to the use of betaine or its physiologically acceptable salt for enhancing endurance during exercise, enhancing muscle mass and reducing muscle soreness and muscle fatigue. It is also directed to the use of betaine or its physiologically acceptable salt for enhancing the flavor of a food or beverage.

31 Claims, No Drawings

USE OF BETAINE TO ENHANCE EXERCISE PERFORMANCE

CROSS REFERENCE TO RELATED APPLICATIONS

This application is a claiming benefit of U.S. Provisional Application Ser. No. 60/343,623 filed Oct. 22, 2001.

FIELD OF THE INVENTION

The present invention relates to a method of enhancing the physical capacity of a mammal involved in muscular exertion by administering to the mammal betaine or its physiologically acceptable salt.

BACKGROUND OF THE INVENTION

Athletes who participate in sports at any level, amateur or professional, strive to bring their bodies to a physical state which is optimum for the sport or activity of interest. One factor which enables athletes to participate effectively is a high degree of development of the aerobic capacity and/or strength of skeletal muscle.

Both aerobic capacity and strength, especially the latter, is a function of training and of muscle mass. These in turn require net synthesis of proteins in the muscle. Strenuous exercise is an effective stimulus for protein synthesis. However, muscles require a large array of nutrients, including amino acids (which are derived from protein) for protein synthesis. These nutrient substrate have been supplied by ingesting diets which provide the necessary amounts of protein, calories, and other nutrients.

The desire to attain, in a rapid manner, the maximum degree of skeletal muscle adaption to exercise has led some athletes to resort to the use of drugs. Such drugs, particularly steroids, are known to "force" muscle growth (protein synthesis) to degrees greater than can be achieved by exercise and diet alone. The use of such drugs is both illegal and dangerous. The use of steroids causes the body to be in a constant anabolic state. The side effects of steroids are dangerous and unacceptable.

Thus, it is desirable to apply training programs which employ a combination of specific exercise technique and a diet without steroids which will enhance the stamina of the individual for exercise, enhance the body mass, and decrease fatigue. The present inventors have found that the use of betaine or its physiologically acceptable salt achieves these objectives plus, in addition, has several advantages.

Betaine is widely distributed in plants and animals, and is a natural component of many foods, including cereals (e.g., wheat, oat), seafood (e.g., shrimp, salmon) and vegetables (e.g., spinach, mushroom). It is also found in sugar beets. Also known as trimethylglycine, it has a molecular weight of 117.15 g/mole. Together with L-glutamine, betaine forms the major component of nitrogen compounds in sugar beets that are soluble in water. Betaine has been known for over a hundred years; in 1866 for example, betaine was isolated from concentrated juices of Beta vulgaris (sugar beet).

Betaine has been used clinically for liver disease. Betaine has been found useful in other applications. For instance, it has been discovered that betaine plays an important role in life maintaining processes in nature. For example, various microorganisms depend upon betaine for their survival. Betaine is important for the control of respiration, osmoregulation, and nitrogen fixation of several useful bacteria. The function of useful microbes in soil that fix atmospheric nitrogen necessary for plants to grow is stimulated by betaine.

It has been found that betaine does not possess any skin irritating properties when used in cosmetics, improves the skin compatibility thereof and has moisturizing properties. Betaine has beneficial effects in toothpaste; it appears that betaine not only reduces the skin-irritating effects of toothpaste components, but also is useful for relieving the symptoms in patients with dry mouth.

Betaine is a lipotropic agent. It increases the level of beneficial SAMe (S-adenosyl-methionine) in the liver, and enables the liver to metabolize fat and protect against many challenges, such as alcohol induced cirrhosis. It also decreases bilirubin and alkaline phosphatase and several other liver enzymes related to a large variety of liver disorders. In addition, it appears to have a key role in protecting kidney cells against highly osmotic urine. Further, its biochemical derivative formed in the liver, dimethylglycine, is known to enhance immune response.

Although betaine has been known for over a century, no one heretofore has suggested or used betaine for the enhancement of an individual performance during exercise, that is, to enhance stamina to participate in exercising, especially strenuous exercise. The present inventors have found that the administration of betaine or its physiologically acceptable salts promotes muscle adaption to strenuous exercise.

BRIEF SUMMARY OF THE INVENTION

The present invention is directed to a method for enhancing the physical performance of a mammal during exercise which comprises administering to the mammal an effective amount of betaine or its physiologically acceptable salt.

DETAILED DESCRIPTION OF THE INVENTION

As described hereinabove, an embodiment of the present invention is to use betaine or physiologically acceptable salts thereof for the enhancement of the stamina and physical performance of a mammal during exercise.

Betaine is trimethylglycine. Betaine may exist in two different forms, as drawn hereinbelow:

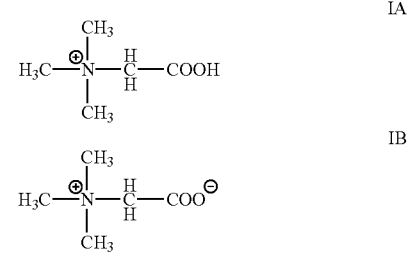

Compound IA is a cationic form, while Compound IB is a zwitterion. Betaine can exist in either form, depending upon the pH. For example, if betaine is placed in strongly acidic medium, betaine will have the formula as depicted in Formula IA. On the other hand, if betaine is placed in basic solutions, it will exist as depicted in Formula IB.

In Formula IA, the betaine will be associated with negatively charged anion. Any physiologically acceptable anion can be associated therewith. Thus, betaine or its physiologically acceptable salts may be administered to the individual in accordance herewith and achieve the efficacious results as described herein.

The expression "physiologically acceptable salt" refers to non-toxic inorganic salts. They include such physiologically acceptable basic addition salts such as bicarbonate, carbonate, hydroxide, halides, such as chlorides, bromides, and the like, anions of organic acids, such as oxalates, citrates, and the like.

In addition, other forms of betaine may be used. They include but are not limited to betaine anhydride, betaine monohydrate, betaine hydrochloride, betaine sodium aspartate, betaine citrate and the like and combinations thereof. In addition, another form of betaine includes carboxylic acid derivatives thereof, such as for examples esters of betaine which can be easily hydrolyzed in vivo. Examples include but are not limited to alkyl esters, wherein alkyl contains 1-6 carbon atoms, aryl esters wherein aryl consists of aromatic ring containing 6-18 ring carbon atoms and up to a total of 24 carbon atoms, aryl alkyl esters, wherein aryl and alkyl are as defined hereinabove, and the like. All of these various forms are contemplated to be within the scope of the term "betaine". However, when referring to a compound of Formula IA or IB, the term "trimethylglycine" will be used. The term betaine will include trimethylglycine. It is preferred that the betaine used is a compound of Formula IA or IB (trimethylglycine) or its physiologically acceptable salt. The anhydrous form of betaine, however, is more preferred. It is also most preferred that the betaine or trimethylglycine utilized is substantially pure.

The betaine used herein is either commercially available or can be prepared from techniques that are described in publications.

In accordance with the present invention, the betaine is administered to mammals. The term mammals refers to a warm blooded animal from the class. Mammalia which is characterized by live birth, body hair and mammary glands in the female that secrete milk to nourish their young. Examples include cats, dogs, mice, rats, horses, cows, monkeys, humans, and the like. It is preferred, however, that the betaine is administered to humans. The terms "subject", and "individual" are synomous with each other and with the term "human," as used herein and have been used interchangeably with the term "human".

Betaine or its physiologically acceptable salt may be administered in solid or liquid form and may include tablets, capsules powders and the like. Oral administration may include the betaine or its physiologically acceptable salt admixed in a carrier fluid appropriate therefor so that it is administered as a liquid (solution or suspension) that is drunk. When the betaine or physiologically acceptable salt is admixed in a carrier fluid, appropriate fluids include, but are not limited to water, rehydration solutions (i.e., water with electrolytes, e.g., potassium or sodium salts, including salts of organic mono-acids or diacids, e.g., citrates), nutritional fluids (e.g., milk, fruit juice coffees, soft drinks, sports drink, and the like), and the like, and combination thereof. The betaine or its physiologically acceptable salt may be admixed with a diet or vitamin supplement or it may be admixed with a drug in a pharmaceutical composition. The betaine formulations may additionally include various adjuvants, such as excipients, as well as other conventional additives for improving disintegration, slow release, absorption, stability and the like. Desirably, the subject compositions will be included in a food substance, which may be either liquid or solid. Thus, the subject composition may be included and is preferably included in a drink or beverage, particularly a soft drink or sports drink which may comprise electrolytes, flavorings, sweeteners or other components to enhance the organoleptic properties of the drink. Examples include GATORADE®, POWERADE®, KOOLAID®, soft drinks, coffee, milk, and the like. Alternatively, the subject formulation may be introduced into various solid foods, for example, health foods which are low in cholesterol, e.g., cereals, (e.g., granola, corn flakes, wheat flakes, and the like), health bars, including fruit bars (date bars, fig bars, apricot bars), and the like.

It is contemplated within the scope of the present invention that additional ingredients, i.e., adjuvants, such as various excipients, carriers, surfactants, nutriments, anti-oxidants, electrolytes (e.g., organic or mineral electrolytes, such as salts) or combination thereof be additionally present in the foods and/or beverages or drinks to which the betaine is added. If it is in solid form such as pill, capsules or tablet, other conventional additives for improving, disintegration, stability, slow release and the like may be present.

A suitable amount of betaine or its physiologically acceptable salt for administration to the mammal is an amount effective to enhance the stamina when it exercises. It is preferred that the betaine or its physiologically acceptable salt is administered daily. In addition, it is preferred that the amounts ingested by the mammal ranges from about 50 mg to about 30 g per 70 kilogram of body weight of the mammal per day and more preferably from about 100 mg to about 20 grams per 70 kilogram of body weight of the mammal per day and most preferably from about 1 gram to about 5 grams per 70 kilogram of body weight of the mammal per day. It may be taken as a single daily dose, or split into several doses. If it is formulate into a capsule, pill or tablets, it may be in the form of immediate or sustained release. Of course, the amount may vary depending on various factors, such as the health of the mammal, the age of the mammal, the environmental conditions, such as temperature, humidity and the like. However, it is most effective when administered to healthy mammals.

When given in the amounts indicated herein, the mammal will experience the effects and advantages described herein when exercising. For example, it may be administered to athletes, e.g., weight lifters, ball players and the like to enhance their physical performance in sports activities; it may be administered to manual laborers, such as a construction worker, a landscaper and the like to enhance their physical performance, and the like. The benefits described herein will also be realized by someone who is out of shape and occasionally performs exercise as well as someone who participates in a regular exercise regimen. In a preferred embodiment, especially when enhancing muscle mass, the mammal also participates in a daily or substantially daily activities (as defined hereinbelow), such as a sports activity, exercise, or manual labor, wherein during each activity, such as exercise sessions or sports performance or manual labor, the mammal exerts enough energy for sufficient time for the body to work up a sweat. The form or time of the activity is not critical as long as the activity results in the body sweating as a result thereof. In one embodiment, the mammal may engage in physical activity for at least about 15 to about 20 minutes at least three or four times a week and more preferably for at least that amount of time at least five times a week and most preferably for at least about 15 to about 20 minutes daily. It is most preferred that the mammal perform the physical activity, e.g., exercise or perform manual labor for at least thirty minutes per day and most preferably at least 45 minutes per day.

It is preferred that the betaine or its physiologically acceptable salt in the above indicated amounts will be taken within 24 hours of the physical activity, e.g., exercise sports activity, manual labor and the like. It may be taken prior to or subsequent to the activity. Preferably, it is taken prior to the activity.

Generally, it will be taken within 24 hours of the activity and may be taken within 6 hours of the activity and more preferably within 3 hours of the activity.

As used herein, the term "activity" refers to an vigorous or energetic act by the mammal that requires physical endurance. For example, it may be an act in which the body incurs an oxygen debt and/or in which there is an enhanced increase in respiration relative to a resting state. As used herein, the term "activity" encompasses exercise, manual labor, and the like.

Exercise, as defined herein, is the repeated use or activity of a muscle group or organ. Exercise is bodily exertion for the sake of developing and maintaining physical fitness. There are two types of exercise, aerobic exercise and anaerobic exercise. An anaerobic exercise occurs when the activity results in the body incurring an oxygen debt. In contrast, aerobic exercise is physical conditioning involving exercise that does not cause an oxygen debt, such as distance running, jogging, walking, swimming, circuit training or cross country skiing strenuously performed so as to cause a marked, but steady increase in respiration and heart rate over an extended period of time. Examples of an anaerobic exercise include weight lifting, handball, football and tennis.

In accordance with the subject invention, by administering the betaine or its physiologically acceptable salt in effective amounts in accordance herewith, exercise and athletic performance, aerobic capacity and muscular output are enhanced. Muscle performance is also improved.

When the betaine or its physiologically acceptable salt is given in effective amounts in accordance with the present invention, as described herein, the stamina of the animal for activity, including exercise, is enhanced. It has more energy to perform the activity. It enables the mammal to expend more energy during the activity and/or to complete the activity. For example, the mammal has the stamina and energy to run the treadmill at a particular speed for a significantly longer time. Alternatively, he may increase his running speed for the same length of time. Thus, the administration of betaine or its physiologically acceptable salt in accordance with the present invention improves peak muscle performance and extends the endurance of the mammal.

Moreover, the administration of betaine or its physiologically acceptable salt, in the amounts described herein, enhances the mammals activity, e.g., exercise capacity. Exercise capacity is limited by the rate by which oxygen can be taken up by a host. When betaine or its physiologically acceptable salt is administered to the mammal in accordance with the present invention, the oxygen uptake, including the rate of oxygen uptake (aerobic metabolism) as well as anaerobic metabolism (oxidation of sugar in the absence of oxygen to produce lactic acid or lactate) is enhanced relative to a state wherein betaine is not administered.

When the betaine or its physiologically acceptable salt is administered to the mammal in accordance with the present invention, the $VO_2$ level achieved is higher than if it were not ingested. For instance, the uptake of oxygen is higher if the individual participated in an exercise regimen, as described herein and ingested betaine or its physiologically acceptable salt in the amounts described herein than if the individual participated in an exercise regimen without it being administered.

Moreover, when administered in the amounts described hereinabove, the betaine or its physiologically acceptable salt, helps to maintain the water balance.

It is well known that, during certain activity, e.g., manual labor, exercise and the like, the body loses fluid and nutrients that must be replenished. Prolonged activity affects the body water's balance due to increased water loss through sweating. Water balance is further strained if the ambient temperature during the activity is high, increasing the need for evaporative cooling, for example only, about a third of chemical energy burned during exercise is converted into mechanical energy, with the remainder of energy burned into heat. Heat dissipation occurs primarily through sweating; about 1 liter of water per hour is typically lost in sweat. This may increase to 1.5 to 2.0 liters per hour with strenuous exercise, particularly in high ambient heat. Thus, after physical exertion during an activity, e.g., exercising, the mammal should normally ingest water, preferably with essential electrolytes to respond to this deficit. Moreover, besides water loss, sweating which accompanies the activity or exercise, results in loss of electrolytes. For example, sodium and chloride are the major electrolytes in sweat and plasma. The concentrations in sweat in a human, e.g., is $50.8 \pm 15.4$ millimoles of sodium and $46.6 \pm 13.1$ mM chloride, which is approximately one third the concentration in plasma.

However, the administration of betaine or its physiologically acceptable salt in the accordance with the present invention, helps to regulate water balance and protects the body from damage due to excessive loss of water or change in the electrolyte concentration. On the other hand, if too much water is ingested, the concentration of the electrolyte in the plasma decreases, which if decreased a sufficient amount, may result in dire consequences to the mammal. The administration of betaine or its physiologically acceptable salt in the amounts described herein helps to regulate the electrolyte concentration and osmotic pressure so that the body can still function normally even if there is a change in the amount of water or electrolyte concentration in the plasma. In addition, the use of betaine or its physiologically acceptable salt in amounts described herein, in accordance with the present invention also protects or retards the break-down of protein, even when there is a high water loss due to sweating.

Without wishing to be bound, it is believed that the betaine or its physiologically acceptable salt is acting as an osmolyte and is alleviating the dehydration, e.g., resulting from exercise. As used herein, the term "osmolyte" refers to a compound which is a solute in body fluids, circulates in an animal, enters cells in response to changes in osmotic milieu, and protects the cell from damage due to excessive loss or uptake of water.

In another embodiment, the administration of betaine or its physiologically acceptable salt retards and/or prevents dehydration, and/or facilitates hydration. The administration of betaine or its physiologically acceptable salt alleviates and/or relieves environmental stress which affects physical capabilities. For instance, in a hot climate, especially hot and humid climate, the body tends to sweat, even when it is not engaged in any physical activity. This is further exacerbated when the mammal engages in physical activity. However, the administration of betaine or its physiologically acceptable salt in the amounts described herein, in accordance with the present invention, will retard and/or prevent the loss of water through sweating and/or decrease the amount of sweat under these environmentally stressed conditions.

Another advantage of the use of betaine or its physiologically acceptable salt in the amounts described herein is the enhancement of muscle mass. Athletes engage in strenuous training. This strenuous training essentially amounts to trauma to the body, in the human body interprets every strenuous work-out as a threat to its survival. It is known that muscle damage, caused by excessive training, releases the catabolic hormone prostaglandin-E2. Strenuous exercise also causes the release of adrenocorticotropin (ACTH), which is a pituitary hormone. The presence of increased levels of ACTH increases the production of the catabolic hormone cortisol, also known as hydrocortisone, which is a naturally occurring anti-inflammatory steroid. The catabolic hormone results in the release of amino acids from muscle tissue and prevents absorption of glucose. Thus, cortisol cannibalizes muscle tissue. High cortisol levels also result in the breakdown of connective tissue, lowers immunity and reduces muscle RNA synthesis. Cortisol may be a detriment to the athlete, however, its presence is useful when a human body is stressed or traumatized. The biological design of cortisol is such that when a human is threatened, cortisol levels rise and mobilize the body for action by breaking down fat and muscle stores for emergency energy. Cortisol also reduce swelling in the event of injury. After the threat or trauma has subsided cortisol levels return to normal. The cortisol-stress relationship is designed for intermittent physical threats and not the constant stimulation provided by today's aggressive athletes. Ongoing training results in cortisol levels that do not return to normal for extended periods of time and thereby results in the breakdown or loss of muscle tissue.

After strenuous exercise, muscle tissue enters a stage of rapid nitrogen absorption in the form of amino acids and small peptides in order to rebuild the muscle fibers and grow and add new muscle fibers.

But, athletes that over-train sometimes enter into a catabolic state. Muscle catabolism occurs when the athlete enters a negative nitrogen balance. The body will thus use energy stores, such as fat and muscle tissue.

However, the administration betaine or its physiologically acceptable salt in effective amounts, as described herein, enhances the muscle mass gain. The consumption of betaine or its physiologically acceptable salts results in an increase in muscle mass. However, if the mammal, e.g., individual also engages in the exercise regimen, as described herein, the growth of muscle mass is further enhanced. Moreover, if in addition to the administration of betaine or its physiologically acceptable salt to the mammal, it ingests a hypercaloric diet with or without physical activity, e.g., exercising manual labor and the like, the growth of muscle mass is also enhanced. A hypercaloric diet is one that will supply an amount of energy beyond that required for a given level of activity. In such a situation, the body will store the excess energy in the form of fat or adipose tissue.

In a preferred embodiment the mammal ingests betaine or its physiologically acceptable salt and a hypercaloric diet and engages in physical activity; this will tend to maximize the growth of the muscle mass.

Without wishing to be bound it is believed that the enhanced energy expenditure described herein is attributable to the breakdown of the fat.

Moreover, to further enhance the muscle mass gain, it is preferred that the mammal engages in the exercise regimen described herein.

Thus, when the betaine is used the amounts described herein, especially when combined with the exercise regimen described herein, substantial gains in the muscle mass (sometimes referred to as increases in protein concentration) in the body of the mammal is achieved.

Without wishing to be bound it is believed that the administration of betaine or its physiologically acceptable salt may increase creatine levels in the body, which may act as an alternate mechanism for the increase in muscle weight gain.

Another advantage of the administration of betaine or its physiologically acceptable salt in effective amounts in accordance with the present invention is the alleviation and/or reduction of delayed or post onset muscle soreness. Administration of betaine or its physiologically acceptable salt in the amounts described herein, in accordance with the present invention, reduces muscle soreness. Delayed or post onset muscle soreness is a feeling of ill-localized pain, tenderness, deep aches and stiffness in muscle that begins after exercise, usually within several hours after exercise is abated. Such soreness may be caused by a sudden mechanical injury or un-accustomed exercise. Such soreness particularly affects inactive individuals after a bout of unaccustomed exercise which involves a significant eccentric component. Eccentric muscle action involves actively resisting the lengthening of the muscle and is characterized by high tension on muscle fibers and connective tissue. The severity of delayed muscle onset soreness is highly variable, ranging from a mild soreness to a debilitating pain which limits muscle usage.

Although the cause of this soreness is not completely known, it is hypothesized, without wishing to be bound, that damage to muscle ultra-structure during unaccustomed exercise initiates an inflammatory response which stimulates intra-muscular pain receptors. Alternatively, without wishing to be bound, it is believed that muscular pain receptors are stimulated or sensitized by other than inflammatory mediators, for example, by intracellular metabolites or by one or more of the by products of proteolysis (for example, histamine, acetyl choline, bradykinen; potassium PGE).

Traditional treatment of muscular or soft tissue injuries involves the application of the so-called "R.I.C.E." principles—rest, ice, compression and elevation. These activities are directed primarily to reducing inflammation, which, as noted above, is a likely cause responsible for muscle soreness. Other treatments include prescription of non-steroidal anti-inflammatory drugs, or more recently anti-prostaglandin medications. The inhibition of prostaglandin production, for example, by drugs, such as acetylsalicyclic acid and ibuprofen, has found to be helpful in reducing muscle soreness. However, these treatments do not completely alleviate delayed onset muscle pain, and many people are averse to taking such medications.

However, since betaine is a natural product, people would not be averse to its administration. Moreover, if the betaine is administered in effective amounts in accordance with the regimen described hereinabove, the muscle soreness is relieved and/or considerably reduced. Thus, the present invention is also directed to a method of alleviating delayed onset muscle soreness in mammals, especially humans. The method comprises administering to the individual, e.g., mammal, an effective amount of betaine or its physiologically acceptable salt.

Thus, the administration of betaine or its physiologically acceptable salt thereof in the amounts indicated herein protects proteins when the mammal performs the activity or exercise.

Another advantage of the present invention is to retard muscle fatigue. It is well known that strenuously exercising muscle burns glucose in a largely anaerobic manner, resulting in the generation of lactate or lactic acid (which is derived directly from pyruvate). Build up of lactate in muscle is associated with muscle fatigue, and is considered to be undesirable. However, the administration of effective amount of betaine or its physiologically acceptable salt in accordance with the procedure described herein reduces muscle fatigue and/or retards the onset of muscle fatigue. It may be administered before or after the physical activity. The administration of betaine or its physiologically acceptable salt in accordance with the present invention, in the amounts described herein, thus has an anti-fatigue effect.

Without wishing to be bound, it is believed that this is attributable to the osmolytic properties of betaine or its physiologically acceptable salt. It is believed that the onset of muscle fatigue or post muscle soreness is attributable to damage to the muscle mass. Without wishing to be bound, it is believed that the betaine or its physiologically acceptable salt in the amounts described herein helps to protect the muscles in mammals. This is especially applicable from damage due to exercise, individuals, who do not regularly exercise and/or are out of shape.

The present invention will be of substantial benefit to all athletes, especially body builders, weight lifters, football players, soccer players, baseball players, and the like, and those individuals who engage in strenuous activity, especially on a daily basis, such as construction workers, laborers, landscapers, and the like.

The following non-limiting examples further illustrate the present invention.

EXAMPLE 1

Ten male subjects were selected to participate in four experimental tests, described below. The study design was a randomized placebo-controlled double blind test. These tests were identical, except that a different rehydration solution was consumed during each session. The rehydration solutions are:

(a) Non-nutritive KOOL-AID®;
(b) Non-nutritive KOOL-AID® and betaine (5 g/l);
(c) GATORADE®; and
(d) GATORADE® and betaine (5 g/l).

The order of treatment for each subject was randomized.

The following measurements were taken before experimental testing to determine the baseline characteristics of the test subject sampled: age, height, body mass and body mass index, percent fat and fat free-mass (%) via skin fold, maximal oxygen consumption.

The following measurements were taken throughout each of the four experimental tests:

1) Hydration variables were measured each day, including urine specific gravity and color, body weight, plasma osmolity.

2) Blood variables were sampled during each trial, including, hematocrit, hemoglobin, osmolality, glucose, lactate.

3) Physiological variables were measured during each trial, such as time to exhaustion (duration of final sprint), heart rate, blood pressure, oxygen consumption, minute ventilation, mean weighted skin temperature, rectal temperature, whole body sweat rate.

4) Perceptual variables were recorded, such as rating of perceived exertion (Borg scale) during the exercise test, thermal stress during the exercise test, thirst sensation during the exercise test.

Prior to the test, baseline descriptives characteristics were measured.

Each subject participated in four experimental tests, performed at the same time of day for each subject, using the same posture at each stage of testing. Experimental tests were randomized. Trials were conducted in an environmental chamber controlled at 30° C.

Starting from 6:00 p.m. the night before the trial until 7:00 a.m. the day of the trial, the subjects did not consume any liquid. When they arrived at the test center at 7:00 a.m., the body weight was measured, a blood sample was taken and the specific gravity of the urine was measured. In general, the subjects were mildly dehydrated, losing approximately 1% body weight. They then ate a standardized breakfast of bagel, cream cheese and banana, but they did not consume any fluids. Subsequently, thereto, they then entered an environmental chamber which was maintained at a temperature of 30° C. and they stood for thirty minutes to effect fluid and thermal equilibration.

Various measurements were taken of each subject including blood pressure, urine specific gravity, body weight, blood pressure, plasma, osmolality and a blood sample when in the environmental chamber prior to the test. Each then performed cycling and walking exercise for 60-90 minutes at 50-55% $VO_{2max}$ so that they each lost about 3% of body weight.

At about 9:30 a.m., they consumed one of the above fluids.

The total volume was ingested in five equal portions over 25 minutes. (This increased the body weight change to a −1.5% level). They each stood an additional twenty minutes to allow gastric emptying. Then they began a treadmill run for 75 minutes at 65% $VO_{2max}$. They finished the exercise in the heat by a sprinting to volitional exhaustion at a treadmill pace that elicits 90% $VO_{2max}$. At the conclusion, they stood in the environmental chamber for additional measurements during a 15 minute recovery period. They left the chamber, then ate a meal and drank fluids.

The test was repeated for each person three more times, except each time they ingested a different one of the fluids so that at the end of the test, each subject had ingested each one of the four fluids. Subjects were instructed to match the diet they ate before the initial experiment, during the three subsequent trials.

Blood samples were taken at various points in each run: (a) baseline, which was at 7:00 a.m. arrival at the test center, (b) following dehydration to −3% (prior to rehydration) at about 9:30 a.m., (c) following rehydration to about −1.5% (prior to exercise), (d) midpoint of a prolonged moderate exercise (35 min. point), (e) end of prolonged moderate exercise (70 min.), prior to final sprint, (f) at the end of sprint to volitional exhaustion, (g) and following 15 min. standing recovery period in heat at approximately 11:45 a.m.

The results were as follows:

(1) When the GATORADE®/betaine mixture was consumed, the sprint time of the subjects was increased 17% longer relative to GATORADE alone. In addition, when the subjects ingested the KOOLAID®/betaine mixture, the sprint time was 9% longer relative to KOOLAID® alone being ingested. In other words, the addition of betaine to the drinks enhanced the stamina of the subject so that he was able to maintain the sprinting for a longer period of time relative to the control.

(2) In the GATORADE® trials, the consumption of betaine resulted in a 6% greater oxygen uptake (aerobic metabolism) while sprinting. Thus, the subjects increased aerobic metabolism. This effect was not seen in the KOOL-AID® trials.

(3) In the GATORADE® trials, betaine resulted in increased plasma lactate levels immediately after the sprint (10%) and 15 minutes after the sprint (17%). Thus, the betaine increased the lactate concentration before exhaustion. This is probably attributable to increased anaerobic metabolism, although it could be caused by decreased lactate clearance from the blood. This effect was not seen in the KOOL-AID® trials.

Betaine has another advantage, it enhances the flavor of the food or beverage to which it is added. More specifically, the present inventors found that when betaine or its physiologically acceptable salts were added in flavor enhancing effective amounts to various foods, especially non-alcoholic drinks, beverages for example, soft drinks, sports drinks, and other types of beverage, in the amounts described herein, it increased the rounding or smoothing of the food, increased the sweetness of the food, decreased the bitterness or astringency, decreased sourness and enhanced masking and decreased the off-taste flavor of the food or beverage to which it was added. To discern this effect, it is preferred that the betaine or its physiologically acceptable salt is added to the food, including drinks or beverages in amounts ranging from about 0.01% to about 5% (w/w) and more preferably from about 0.05% to about 3% (w/w) and most preferably from about 0.1% g to about 0.5% (w/w) by weight of the food, e.g., beverage drink.

Thus, the present invention is also directed to a method of enhancing the flavor of a food, which method comprises adding to the food a taste enhancing flavoring effective amount of betaine or its physiologically acceptable salt. However, the effective amount described herein is a minimum amount to be added. Thus, the amount described herein or greater can be added to the food to enhance its flavor.

This is illustrated in the next example.

EXAMPLE 2

0.1%, 0.5% and 1% betaine (w/w) were added to the following beverages:
(a) Diet soda
(b) Instant coffee
(c) Isotonic solution
(d) 10% raspberry-peach solution
(e) 15% berry juice smoothie
(f) soymilk
(g) grapefruit alcoholic beverage.

The various beverage without any betaine (control) and with the betaine in the levels indicated hereinabove were given to a taste panel and they were asked to indicate which drink they preferred.

Most of the taste panel preferred the taste of a solution of a 0.1% betaine in the isotonic drink, juice (15%) smoothie, coffee (Inst. decaff.), coffee (Inst. reg.) and mocha cappuccino. Most of the panel preferred the taste of 0.5% betaine in one brand of soymilk and diet soda.

They found no difference in another brand of soymilk and 10% juice drink and preferred the alcoholic (5%) beverage without betaine.

Thus, 7 out of the ten beverages tested were preferred with the betaine. The test panel did not prefer the betaine added to the alcoholic beverage; although it changed the taste, the taste testers expected a certain taste for alcoholic beverage, and the betaine/alcohol provided a different taste.

Moreover, betaine addition greatly enhanced the flavor of soda, especially diet soda containing artificial sweeteners; it was noted that in the amounts added to the soda, it smoothed the notes of bitterness of the artificial sweetener.

The present inventors in a separate study, found that the addition of betaine to Powerades such as Mountain Blast® and Arctic Shatter®, enhanced the flavor thereof; the betaine containing solution was preferred by the taste panel by a margin of about 2:1 relative to the control.

Thus, the addition of betaine or its physiologically acceptable salts in the effective amounts indicated herein, exhibited several beneficial effects, such as the reduction of sore muscle, increase of the muscle performance, increase of latent vitality, increase of endurance, enhanced circulation and respiration as well as oxygen supply to the tissue, increased aerobic metabolism and anaerobic metabolism oxygen uptake, to name just a few beneficial results. Furthermore, the addition of betaine or its physiologically acceptable salt maintains homeostasis under duress, such as physical activity, especially when the mammal is near exhaustion, and maintains water and electrolyte balance even under these conditions. Moreover, it enhanced the flavor characteristics of the foods.

It is to be noted that the effective amounts for each of the utilities described herein except for flavor enhancing, are within the same range.

As used herein, the plural denotes the singular and vice versa.

Unless indicated to the contrary, all percentages are by weight.

The above preferred embodiments and examples are given to illustrate the scope and spirit of the present invention. The embodiments and examples described herein will make apparent to those skilled in the art other embodiments and examples. These other embodiments and examples are within the contemplation of the present invention. Therefore, the present invention should be limited only by the appended claims.

What is claimed:

1. A method for enhancing the physical performance of a mammal, said method consisting essentially of administering daily to said mammal an effective amount of betaine or its physiologically acceptable salt prior to said physical performance but within 24 hours of said physical performance, wherein the amount of betaine or its physiologically acceptable salt administered to the mammal ranges from about 50 mg to about 30 g per 70 kilogram of weight of the mammal.

2. The method according to claim 1 wherein the betaine or physiologically acceptable salt thereof is administered as a solid or liquid.

3. The method according to claim 2 wherein the betaine or physiologically acceptable salt thereof is administered in the form of a powder, tablet, capsule, pill, food or liquid.

4. The method according to claim 3 wherein the betaine or physiologically acceptable salt thereof is administered as a beverage.

5. The method according to claim 4 wherein additional adjuvants are present in the beverage.

6. The method according to claim 5 wherein the adjuvants comprise at least one of the following: electrolytes, excipient, surfactant, sugar or anti-oxidant.

7. The method according to claim 1 wherein the betaine or its physiologically acceptable salt is added to a sports drink.

8. The method according to claim 1 wherein betaine or its physiologically acceptable salt is anhydrous.

9. The method according to claim 1 wherein the betaine or its physiologically acceptable salt is administered as a solid.

10. The method according to claim 1 wherein the physical performance is enhanced by increasing the stamina of the mammal.

11. The method according to claim 1 wherein the physical performance is enhanced by increasing the amount of energy output of the mammal.

12. The method according to claim 1 wherein physical performance is enhanced by increasing the muscle mass of the mammal.

13. The method according to claim 1 wherein the betaine or its physiologically acceptable salt is administered within six hours prior to the physical performance.

14. The method according to claim 13 wherein the betaine or its physiologically acceptable salt is administered within three hours prior to the physical performance.

15. A method for enhancing the physical performance of a physical activity by a mammal requiring physical endurance, which consisting essentially of administering daily to said mammal an effect amount of betaine or its physiologically acceptable salt prior to said activity but within 24 hours of said activity, wherein the amount of betaine or its physiologically acceptable salt administered to the mammal ranges from about 50 mg to about 30 g per 70 kilogram of weight of the mammal.

16. The method according to claim 15 where the activity is exercise.

17. The method according to claim 16 wherein the exercise is aerobic exercise.

18. The method according to claim 16 wherein the exercise is anaerobic exercise.

19. The method according to claim 15 wherein the activity is manual labor.

20. The method according to claim 15 wherein the activity is a sports activity.

21. The method according to claim 15 wherein the activity is strenuous physical activity.

22. The method according to claim 15 wherein the activity is performed sufficiently long for the mammal to sweat.

23. The method according to claim 15 wherein the betaine or physiologically acceptable salt thereof is administered as a solid or liquid.

24. The method according to claim 23 wherein the betaine or physiologically acceptable salt thereof is administered in the form of a powder, tablet, capsule, pill, food or liquid.

25. The method according to claim 24 wherein the betaine or physiologically acceptable salt thereof is administered as a beverage.

26. The method according to claim 25 wherein additional adjuvants are present in the beverage.

27. The method according to claim 26 wherein the adjuvants comprise at least one of the following: electrolytes, excipient, surfactant, sugar or anti-oxidant.

28. The method according to claim 15 wherein the betaine or physiologically acceptable salt is administered within six hours prior to the physical performance.

29. The method according to claim 15 wherein the betaine or its physiologically acceptable salt is administered within three hours prior to the physical performance.

30. The method according to claim 15 wherein the betaine or its physiologically acceptable salt is added to water or to a sports drink.

31. The method according to claim 15 wherein the betaine or its physiologically acceptable salt is anhydrous.

* * * * *